US012648692B2

(12) United States Patent
Takahashi et al.

(10) Patent No.: US 12,648,692 B2
(45) Date of Patent: Jun. 9, 2026

(54) OPHTHALMIC APPARATUS, METHOD OF CONTROLLING SAME, AND RECORDING MEDIUM

(71) Applicant: Topcon Corporation, Tokyo (JP)

(72) Inventors: Akira Takahashi, Tokyo (JP); Kazuhiro Yamada, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 721 days.

(21) Appl. No.: 17/894,175

(22) Filed: Aug. 24, 2022

(65) Prior Publication Data

US 2022/0400948 A1 Dec. 22, 2022

Related U.S. Application Data

(63) Continuation of application No. PCT/JP2021/008665, filed on Mar. 5, 2021.

(30) Foreign Application Priority Data

Mar. 13, 2020 (JP) ................................. 2020-043603

(51) Int. Cl.
*A61B 3/00* (2006.01)
*A61B 3/12* (2006.01)
(Continued)

(52) U.S. Cl.
CPC .............. *A61B 3/12* (2013.01); *A61B 3/0008* (2013.01); *A61B 3/0025* (2013.01); *A61B 3/14* (2013.01)

(58) Field of Classification Search
CPC ....... A61B 3/0008; A61B 3/0025; A61B 3/10; A61B 3/1025; A61B 3/12; A61B 3/14; H04N 25/531
See application file for complete search history.

(56) References Cited

U.S. PATENT DOCUMENTS 7,335,898 B2 2/2008 Donders et al.
7,831,106 B2 11/2010 Elsner et al.
(Continued)

FOREIGN PATENT DOCUMENTS

CN 106073697 A 11/2016
CN 114401663 A 4/2022
(Continued)

OTHER PUBLICATIONS

Extended European Search Report issued Feb. 28, 2024, in corresponding European Patent Application No. 21767623.8, 11pp.
(Continued)

*Primary Examiner* — Jack Dinh
(74) *Attorney, Agent, or Firm* — XSENSUS LLP

(57) ABSTRACT

An ophthalmic apparatus includes an illumination optical system, an optical scanner, an imaging optical system, a controller, and an image forming unit. The illumination optical system is configured to generate slit-shaped illumination light. The optical scanner is configured to deflect the illumination light to guide the illumination light to a fundus of a subject's eye. The imaging optical system is configured to guide returning light of the illumination light from the fundus to an image sensor. The controller is configured to control the optical scanner. The image forming unit is configured to form an image of the fundus based on a light receiving result captured in an imaging target region on a light receiving surface of the image sensor. The image sensor is configured to capture the light receiving result in an opening region on the light receiving surface using a rolling shutter method, the opening region corresponding to an illumination region of the illumination light on the fundus, the illumination region being moved in a predetermined scan direction by the optical scanner. The controller is configured to control the optical scanner so that irradiation times of the (Continued)

returning light at a plurality of light receiving elements in the imaging target region are substantially equal.

3 Claims, 11 Drawing Sheets

(51) Int. Cl.
    *A61B 3/14*         (2006.01)
    *G16H 50/20*      (2018.01)

(56) References Cited

U.S. PATENT DOCUMENTS

| | | |
|---|---|---|
| 8,237,835 B1 | 8/2012 | Muller |
| 8,967,806 B2 | 3/2015 | Bublitz et al. |
| 2009/0244482 A1 | 10/2009 | Elsner et al. |
| 2010/0128221 A1 | 5/2010 | Muller et al. |
| 2012/0165905 A1 | 6/2012 | Liesfeld et al. |
| 2013/0093873 A1 | 4/2013 | Bula et al. |
| 2013/0222763 A1 | 8/2013 | Bublitz et al. |
| 2015/0085252 A1 | 3/2015 | Fujimura et al. |
| 2015/0131050 A1 | 5/2015 | Bublitz et al. |
| 2015/0350573 A1 | 12/2015 | Toda et al. |
| 2016/0317028 A1 | 11/2016 | Murata et al. |
| 2016/0345822 A1 | 12/2016 | Fujimura et al. |
| 2022/0313084 A1 | 10/2022 | Kim et al. |

FOREIGN PATENT DOCUMENTS

| | | |
|---|---|---|
| JP | 61-293430 A | 12/1986 |
| JP | 2009-538697 A | 11/2009 |
| JP | 2010-259495 A | 11/2010 |
| JP | 2013-248376 A | 12/2013 |
| JP | 5897563 B2 | 3/2016 |
| WO | 2021049558 A1 | 3/2021 |

OTHER PUBLICATIONS

Japanese Office Action issued Apr. 9, 2024, in corresponding Japanese Patent Application No. 2020-043603, 10pp.
International Search Report and Written Opinion mailed on May 18, 2021, received for PCT Application PCT/JP2021/008665, filed on Mar. 5, 2021, 9 pages including English Translation.
Chinese Office Action issued Feb. 24, 2025, in corresponding Chinese Patent Application No. 202180021265.8, 12pp.

OPHTHALMIC APPARATUS, METHOD OF CONTROLLING SAME, AND RECORDING MEDIUM

CROSS-REFERENCE TO RELATED APPLICATIONS

The present application is a continuation application of International Patent Application No. PCT/JP2021/008665, filed Mar. 5, 2021, which claims priority to Japanese Patent Application No. 2020-043603, filed Mar. 13, 2020, both of which are herein incorporated by reference in their entirety.

FIELD

The disclosure relates to an ophthalmic apparatus, a method of controlling the same, and a recording medium.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired.

For example, U.S. Pat. Nos. 7,831,106, 8,237,835, 7,335, 898, and Japanese Patent No. 5897563 disclose ophthalmic apparatuses configured to pattern-illuminate a subject's eye and to receive returning light thereof using an image sensor, using a rolling shutter method. These ophthalmic apparatuses can acquire images of the subject's eye with a simple configuration, by adjusting the illumination pattern and the timing of light receiving using the image sensor.

For example, Japanese Patent No. 5897563 discloses a line scanning microscope with a scanning unit whose scanning trajectory is controlled so as to have an acceleration portion and a deceleration portion outside the field of view of the sensor unit so that the temporal and spatial synchronization between the illumination side and the light receiving side are satisfied throughout the field of view of the sensor unit.

SUMMARY

One aspect of some embodiments is an ophthalmic apparatus, including: an illumination optical system configured to generate slit-shaped illumination light; an optical scanner configured to deflect the illumination light to guide the illumination light to a fundus of a subject's eye; an imaging optical system configured to guide returning light of the illumination light from the fundus to an image sensor; a controller configured to control the optical scanner; and an image forming unit configured to form an image of the fundus based on a light receiving result captured in an imaging target region on a light receiving surface of the image sensor, wherein the image sensor is configured to capture the light receiving result in an opening region on the light receiving surface using a rolling shutter method, the opening region corresponding to an illumination region of the illumination light on the fundus, the illumination region being moved in a predetermined scan direction by the optical scanner, and the controller is configured to control the optical scanner so that irradiation times of the returning light at a plurality of light receiving elements in the imaging target region are substantially equal.

Another aspect of some embodiments is a method of controlling an ophthalmic apparatus including: an illumination optical system configured to generate slit-shaped illumination light; an optical scanner configured to deflect the illumination light to guide the illumination light to a fundus of a subject's eye; an imaging optical system configured to guide returning light of the illumination light from the fundus to an image sensor, the image sensor being configured to capture a light receiving result on an opening region on the light receiving surface, the opening region corresponding to the illumination region of the illumination light on the fundus, the illumination region being moved in a predetermined scan direction by the optical scanner; and a controller configured to control the optical scanner. The method of controlling the ophthalmic apparatus includes: a control step of controlling the optical scanner so that irradiation times of the returning light at a plurality of light receiving elements in the imaging target region on the light receiving surface of the image sensor are substantially equal; and an image forming step of forming an image of the fundus based on a light receiving result captured in the imaging target region.

Still another aspect of the some embodiments is a non-transitory computer readable recording medium storing a program of causing a computer to execute each step of the method of controlling the ophthalmic apparatus of the above.

DETAILED DESCRIPTION

Figure 1:
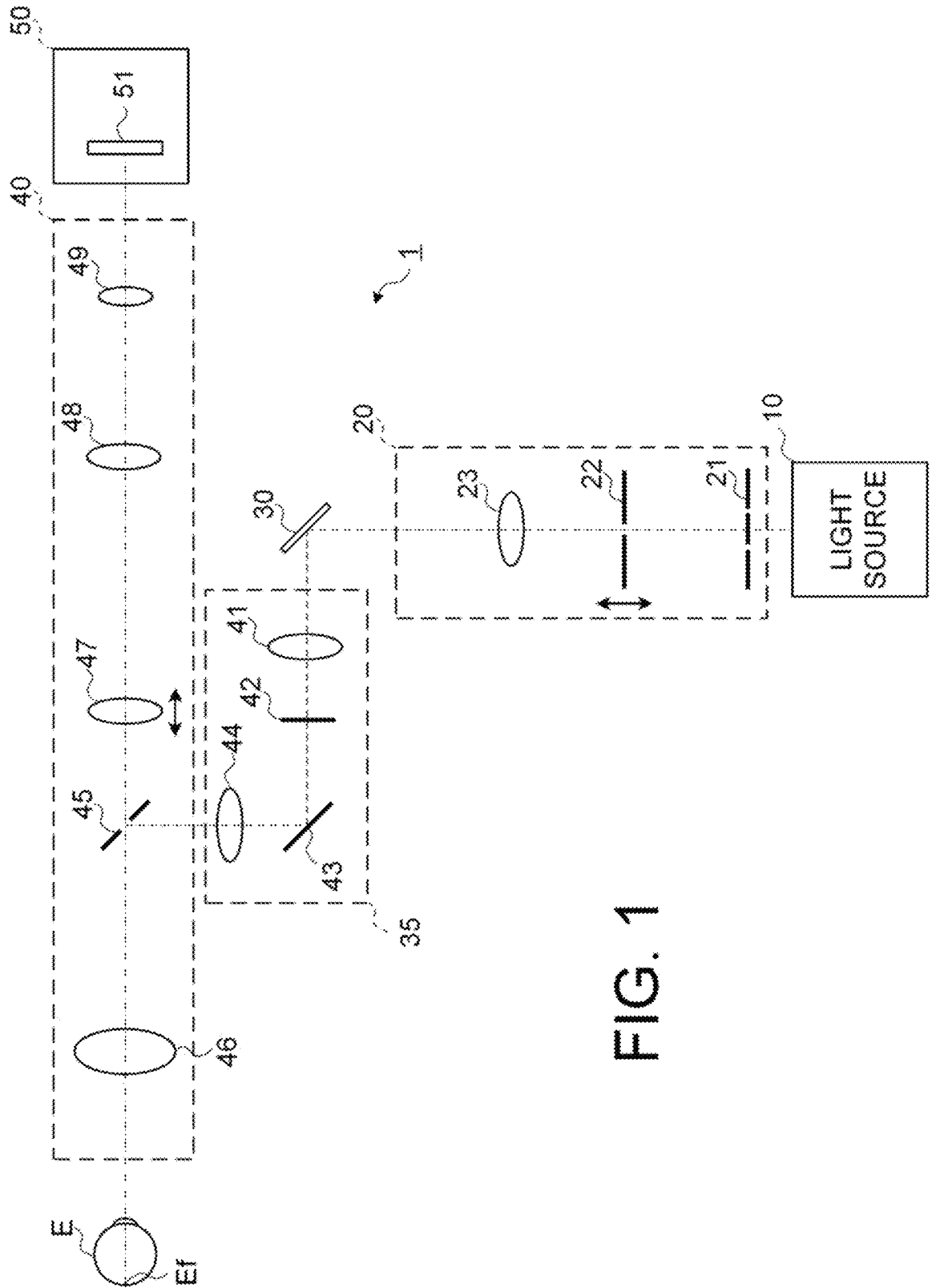
FIG. 1 is a schematic diagram illustrating an example of a configuration of an optical system of an ophthalmic apparatus according to embodiments.

The conventional methods have the problems that the imaging time (shooting time) cannot be shortened, or that even when the imaging time can be shortened, the illumination time varies within the imaging target region in the image sensor.

When the imaging time is long, eye movements, etc. may occur during the imaging. Thereby, it takes a lot of time and effort to re-imaging, etc. When the illumination time varies within the imaging target region, the luminance evenness is generated in the acquired image, resulting in degradation of image quality.

According to some embodiments according to the present invention, a new technique for acquiring a high quality image of a subject's eye in a short imaging time can be provided.

Referring now to the drawings, exemplary embodiments of an ophthalmic apparatus, a method of controlling the same, and a program according to the present invention are described below. The contents of the document cited in the present specification can be appropriately incorporated as contents of the following embodiments.

An ophthalmic apparatus according to embodiments illuminates a predetermined site of a subject's eye while moving an irradiated position (illumination region, irradiated range) of slit-shaped illumination light, and receives returning light from the predetermined site using an image sensor with a one-dimensional or two-dimensional array of light-receiving elements. Light receiving result of the returning light is read out from the light receiving elements at light receiving position of the returning light corresponding to the irradiated position of the illumination light, in synchronization with the movement timing of the irradiated position of the illumination light. In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, a case where the ophthalmic apparatus according to the embodiments acquires images of the fundus of the subject's eye mainly will be described.

[Configuration of Optical System]

Figure 2:
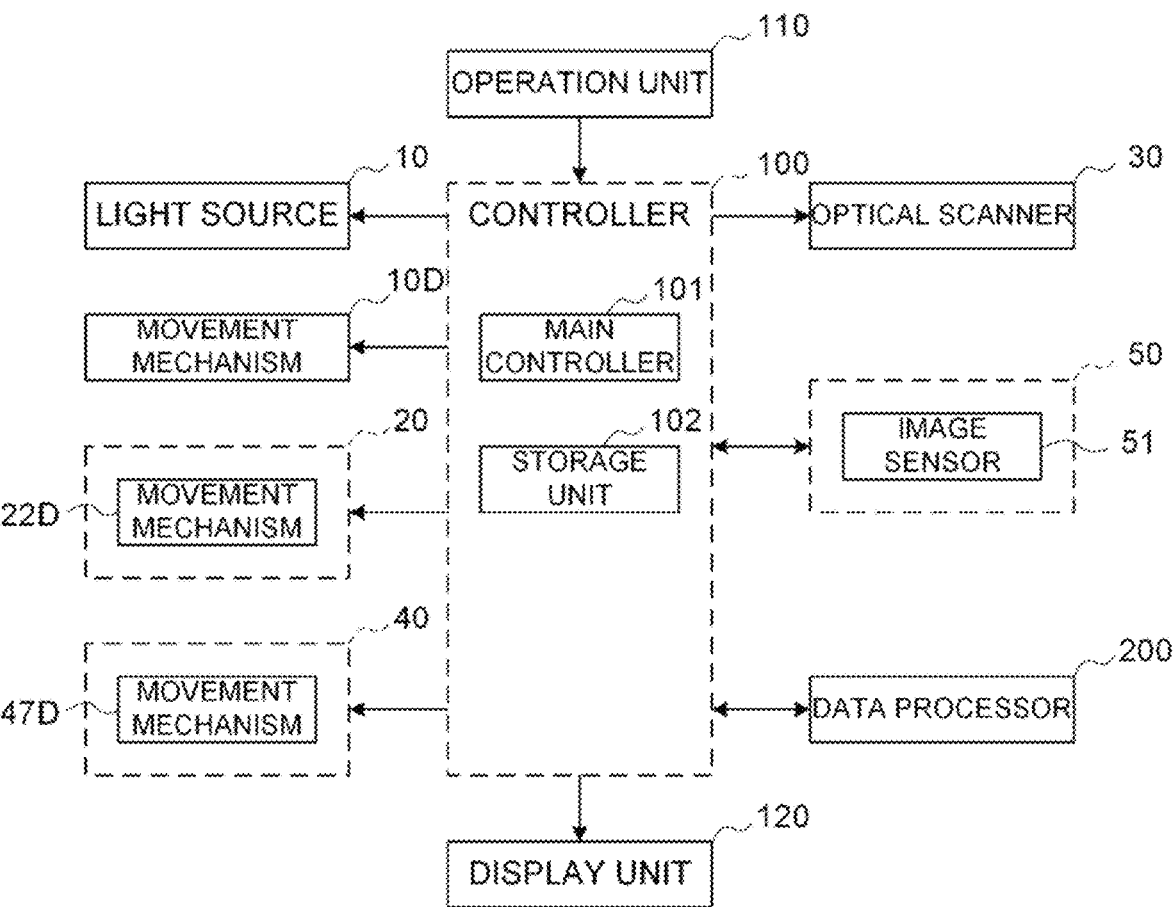
FIG. 2 is a schematic diagram illustrating an example of a configuration of a control system of the ophthalmic apparatus according to the embodiments.
Figure 3:
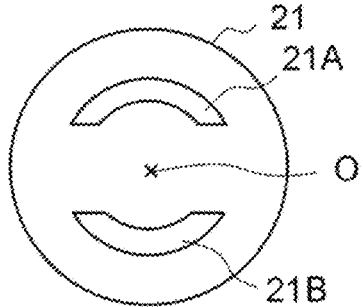
FIG. 3 is a schematic diagram illustrating an example of a configuration of an optical system of the ophthalmic apparatus according to the embodiments.

FIGS. 1 to 3 show schematic diagrams of an example of a configuration of an ophthalmic apparatus according to embodiments. FIG. 1 represents an example of a configuration of an optical system of the ophthalmic apparatus 1 according to the embodiments. FIG. 2 representing a block diagram of an example of a configuration of a control system (processing system) of the ophthalmic apparatus 1 according to the embodiments. FIG. 3 schematically represents an example of the configuration of an iris aperture 21 in FIG. 1 when viewed from a direction of an optical axis O. In FIGS. 1 to 3, like parts are designated by like reference numerals as in repetitious description of such parts may not be provided.

The ophthalmic apparatus 1 includes a light source 10, an illumination optical system 20, an optical scanner 30, a projection optical system 35, and an imaging optical system 40, and an imaging device 50. In some embodiments, the illumination optical system 20 includes at least one of the light source 10, the optical scanner 30, or the projection optical system 35. In some embodiments, the imaging optical system 40 includes the imaging device 50. In some embodiments, the projection optical system 35 or the imaging optical system 40 includes the optical scanner 30.

(Light Source 10)

The light source 10 includes a visible light source that generates light in the visible region. For example, the light source 10 generates light having a central wavelength in the wavelength range of 420 nm to 700 nm. This type of light source 10 includes, for example, an LED (Light Emitting Diode), an LD (Laser Diode), a halogen lamp, or a xenon lamp. In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to each of a fundus Ef and the iris.

(Illumination Optical System 20)

The illumination optical system 20 generates slit-shaped illumination light using the light from the light source 10. The illumination optical system 20 guides the generated illumination light to the optical scanner 30.

The illumination optical system 20 includes the iris aperture 21, the slit 22, and a relay lens 23. The light from the light source 10 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s) away from the optical axis O. For example, as shown in FIG. 3, apertures 21A and 21B having a predetermined thickness along a circumferential direction centered with the optical axis O are formed in the iris aperture 21. The aperture(s) formed in the iris aperture 21 defines an incident position (incident shape) of the illumination light on the iris of the subject's eye E. For example, when the pupil center of the subject's eye E is arranged on the optical axis O, the illumination light can enter into the eye from positions deviated from the pupil center (specifically, point-symmetrical positions centered on the pupil center), by forming the apertures 21A and 21B as shown in FIG. 3.

Further, the light amount distribution of the light passing through the aperture(s) formed in the iris aperture 21 can be changed by changing a relative position between the light source 10 and the aperture(s) formed in the iris aperture 21.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E.

The slit 22 can be moved in the optical axis direction of the illumination optical system 20 using a movement mechanism (movement mechanism 22D described below). The movement mechanism moves the slit 22 in the optical axis direction, under the control from the controller 100 described below. For example, the controller 100 controls the movement mechanism in accordance with the state of the subject's eye E. This allows to move the position of the slit 22 in accordance with the state of the subject's eye E (specifically, the dioptric power or the shape of the fundus Ef).

In some embodiments, the slit 22 is configured so that at least one of the position of the aperture or the shape of the aperture can be changed in accordance with the state of the subject's eye E without being moved in the optical axis direction. The function of the slit 22 with this configuration is, for example, realized by a liquid crystal shutter.

The light from the light source 10 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined illumination range of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20. Examples of scan mode for moving the irradiated position of the illumination light using the optical scanner 30 include a horizontal scan, a vertical scan, a cross scan, a radial scan, a circle scan, a concentric scan, and a helical (spiral) scan.

(Projection Optical System 35)

The projection optical system 35 guides the illumination light deflected by the optical scanner 30 to the fundus Ef of the subject's eye E. In the embodiments, the projection optical system 35 guides the illumination light deflected by the optical scanner 30 through an optical path coupled with an optical path of the imaging optical system 40 by a perforated mirror 45 as the optical path coupling member described below.

The projection optical system 35 includes a relay lens 41, a black point plate 42, a reflective mirror 43, and a relay lens 44. Each of the relay lenses 41 and 44 includes one or more lenses.

(Black Point Plate 42)

The black point plate 42 is arranged at a position substantially conjugate optically to a lens surface of an objective lens 46 or the vicinity of the lens surface of the objective lens 46. This prevents the reflected light from the lens surface of the objective lens 46 from being guided to the light source 10 (illumination optical system 20).

With such projection optical system 35, the illumination light deflected by the optical scanner 30 is transmitted through the relay lens 41, passes through the black point plate 42, is reflected by the reflective mirror 43 toward the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, a focusing lens 47, a relay lens 48, and an imaging lens 49. Each of relay lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the projection optical system 35 toward the objective lens 46, on the peripheral region of the hole.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, and is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can output the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result acquired by the image sensor 51 is read out using a rolling shutter method. In some embodiments, the controller 100 described below performs readout control of the light receiving result by controlling the image sensor 51. In some embodiments, the image sensor 51 can automatically output the light receiving results for a predetermined number of lines, along with information indicating the light receiving position(s).

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. No. 8,237,835.

Figure 4:
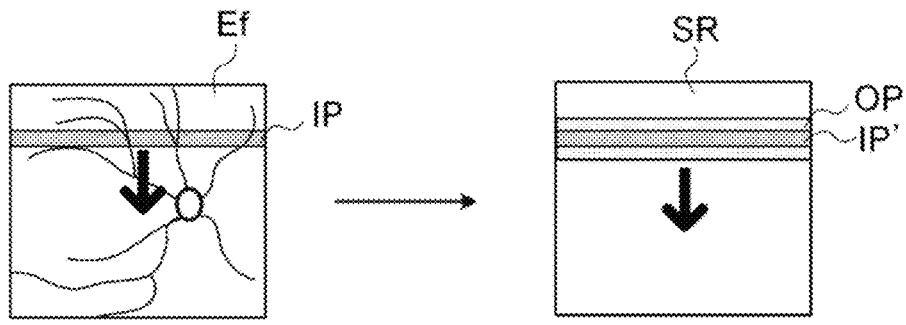
FIG. 4 is an explanatory diagram of an operation of the ophthalmic apparatus according to the embodiments.

FIG. 4 shows a diagram explaining the operation of the ophthalmic apparatus 1 according to the embodiments. FIG. 4 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved (shifted) in a direction (for example, the vertical direction) orthogonal to the slit direction (for example, the row direction, the horizontal direction) on the fundus Ef.

On the light receiving surface SR of the image sensor 51, for example, by changing the pixels to be captured in units of lines by the controller 100 described below, the virtual opening range (opening region) OP is set. The opening range OP is preferable to be the light receiving range IP' of the returning light of the illumination light on the light receiving surface SR or wider than the light receiving range IP'. For example, the controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

Figure 5:
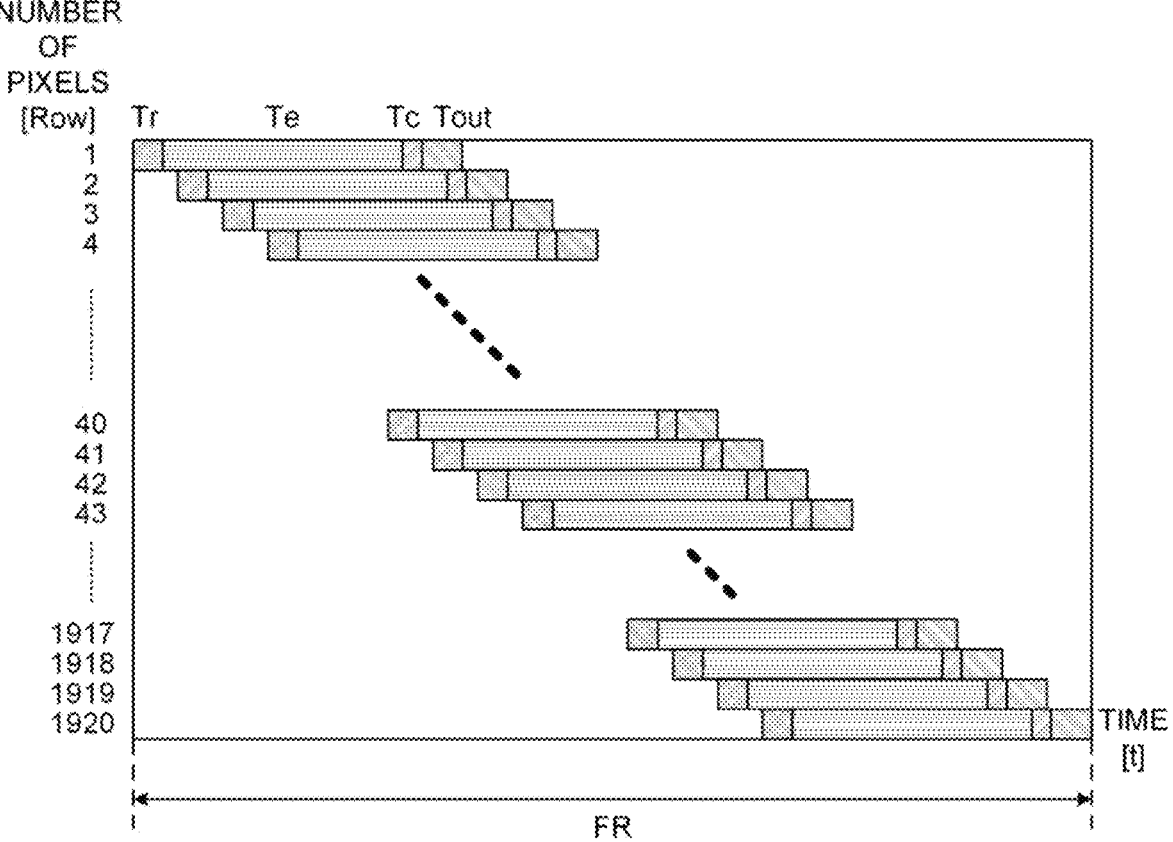
FIG. 5 is an explanatory diagram of the operation of the ophthalmic apparatus according to the embodiments.
Figure 6:
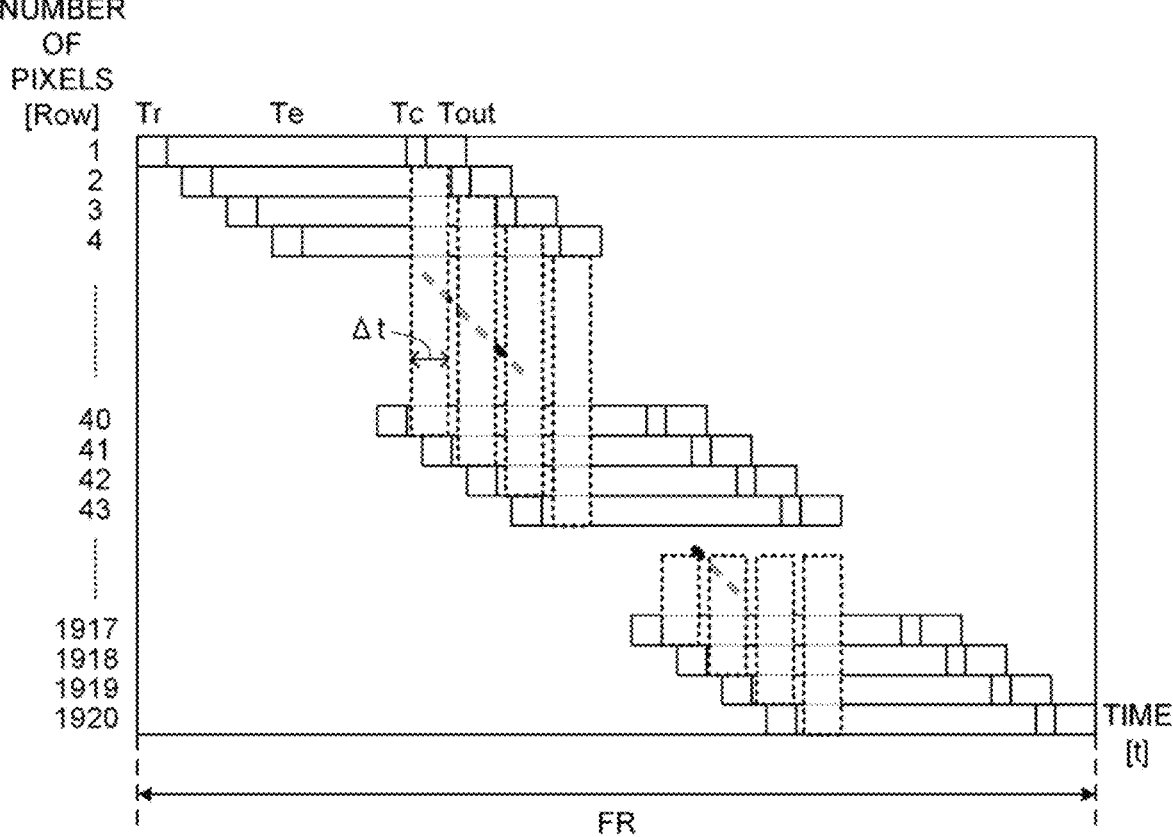
FIG. 6 is an explanatory diagram of the operation of the ophthalmic apparatus according to the embodiments.

FIGS. 5 and 6 schematically show examples of the control timing of the rolling shutter method for the image sensor 51. FIG. 5 represents an example of the timing of the readout control for the image sensor 51. FIG. 6 represents the timing of the movement control for the irradiated range IP (the light receiving range IP') superimposed on the timing of the readout control in FIG. 5. In FIGS. 5 and 6, the horizontal axis represents the number of rows in the image sensor 51, and the vertical axis represents time.

In addition, in FIGS. 5 and 6, for convenience of explanation, it is assumed that the number of rows in the image sensor 51 is 1920. However, the configuration according to the embodiments is not limited to the number of rows. Further, in FIG. 6, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 5, the readout time T for reading out the electrical charge accumulated in the pixels in the row direction is the sum of the time Tr required for the reset control, the time Te required for the exposure control (exposure time), the time Tc required for the charge transfer control, and the time Tout required for the output control.

In FIG. 5, by shifting the readout (capturing) start timing (start timing of time Tc) in units of rows, the light receiving results (amount of electrical charge) accumulated in the pixels in the desired range in the image sensor 51 are acquired. For example, in case that the pixel range shown in FIG. 5 is for a single frame of the image, the frame rate FR is determined uniquely.

In this embodiment, the irradiated position of the illumination light on the fundus Ef, the illumination light having a slit width for a plurality of rows, is sequentially shifted in a direction corresponding to the column direction on the fundus Ef. When the width in the shift direction of the irradiated range IP' (a region corresponding to the illumination region on the fundus Ef) on the light receiving surface of the image sensor 51 has two or more rows, the controller 100 described below controls the optical scanner 30 so that the opening range OP (opening region) shifts in the shift direction in units of a predetermined number of rows.

For example, as shown in FIG. 6, at each predetermined shift time Δt, the irradiated position of the illumination light on the fundus Ef is shifted in row units in the direction corresponding to the column direction. The shift time Δt is obtained by dividing the exposure time Te of the pixel in the image sensor 51 by the slit width (e.g., the number of rows of the slit width=40) of the illumination light (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 51 is configured using one or more line sensors.

By the way, in the method shown in FIG. 6, variations in the irradiation time of the returning light of the illumination light occur for the entire region of the light receiving surface in the image sensor 51. Specifically, the pixel group in the first part in the shift direction of in irradiated region of the illumination region (pixels in the row direction between the 1st row and the 39th row) and the pixel group in the last part in the shift direction (pixels in the row direction between the 1881th row and the 1920th row) have different irradiation times of the returning light of the illumination light compared to the other pixel groups.

Therefore, in the embodiments, it is desirable for the controller 100 described below to control the optical scanner 30 so that the irradiation times of the returning light at a plurality of pixels (light receiving elements) in the imaging target region on the light receiving surface of the image sensor 51 are substantially equal.

Figure 7:
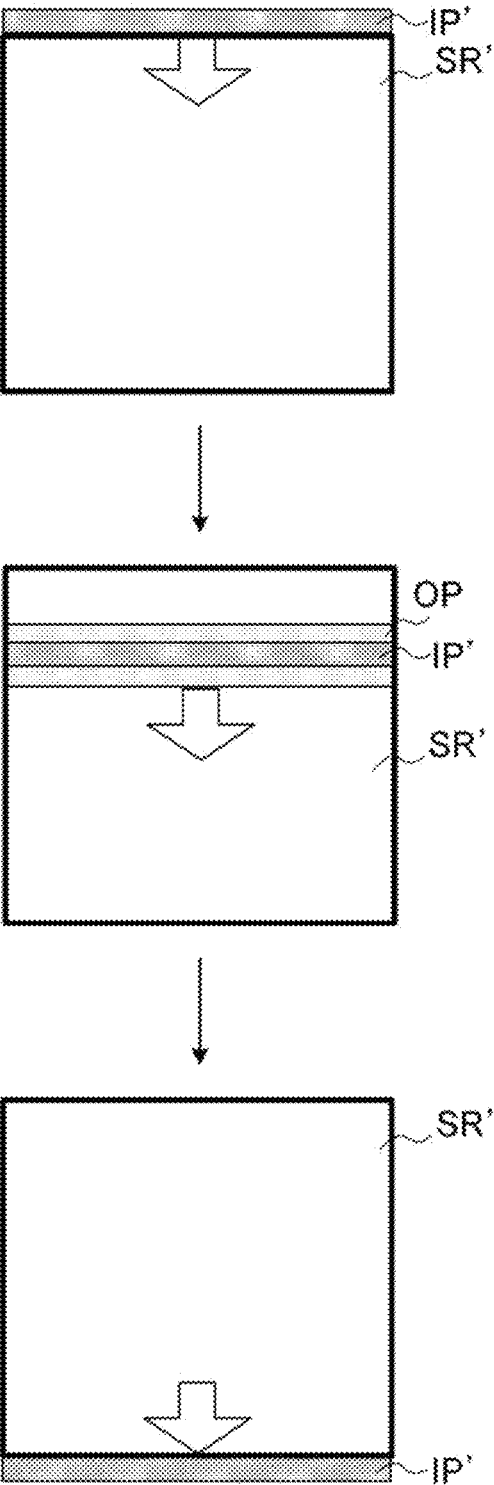
FIG. 7 is an explanatory diagram of the operation of the ophthalmic apparatus according to the embodiments.

FIG. 7 shows a diagram explaining the operation of the ophthalmic apparatus 1 according to the embodiments. FIG. 7 schematically represents an irradiated range on the light receiving surface of the image sensor 51.

For example, as shown in FIG. 7, when an imaging target region SR' is provided in a region of the light receiving surface SR of the image sensor 51 and an image of the fundus Ef is acquired using the light receiving results of the pixels in the imaging target region SR', the irradiated range IP' is made to shift from outside the imaging target region SR'. In other words, the controller 100 described below controls the optical scanner 30 so that the irradiated range IP' shifts from outside the imaging target region SR' as shown in FIG. 6. This allows to reduce the variations (fluctuations) in the irradiation time of the returning light of the illumination light to the plurality of pixels in the imaging target region SR'.

In some embodiments, the controller 100 described below controls the optical scanner 30 so that the irradiated range IP' shifts from outside the imaging target region SR' by a width for at least 1 row. This allows to reduce the variations in the irradiation time of the returning light of the illumination light to the pixel groups in the imaging target region SR', compared to the method shown in FIG. 6.

In some embodiments, the controller 100 described below controls the optical scanner 30 so that the irradiated range IP' shifts from outside the imaging target region SR' by an amount corresponding to the width in the shift direction of the irradiated range IP' on the light receiving surface of the image sensor 51, as shown in FIG. 6.

Figure 8:
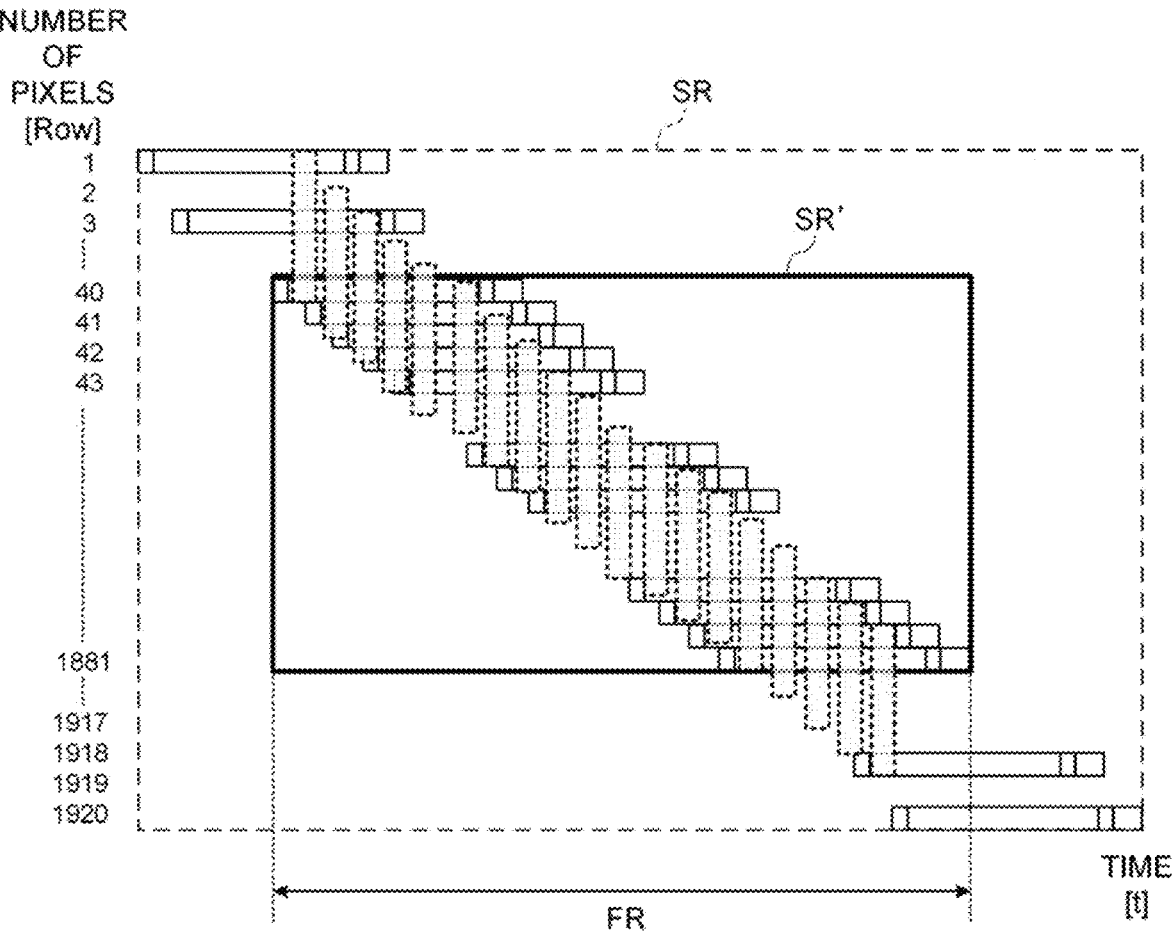
FIG. 8 is an explanatory diagram of the operation of the ophthalmic apparatus according to the embodiments.

FIG. 8 schematically shows an example of the control timing of the rolling shutter method for the imaging target region SR' on the light receiving surface SR of the image sensor 51. In FIG. 8, like reference numerals designate like parts as in FIG. 6 or FIG. 7. The same description may not be repeated. It should be noted that, for convenience of explanation, it is assumed that the slit width (width in the row direction) of the slit-shaped illumination light is 40 rows, also in FIG. 8.

As shown in FIG. 8, the controller 100 described below controls the optical scanner 30 so that the irradiated range IP' shifts from outside the imaging target region SR' by the width in the shift direction (width for 40 rows) of the irradiated range IP' on the light receiving surface of the image sensor 51, as shown in FIG. 6. This allows to make the variations in the irradiation time of the returning light of the illumination light for all pixels groups in the imaging target region SR' substantially equal.

[Configuration of Control System]

As shown in FIG. 2, the control system of the ophthalmic apparatus 1 is configured with a controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the light source 10, control for a movement mechanism 10D, control for the illumination optical system 20, control for the optical scanner 30, control for the imaging optical system 40, control for the imaging device 50, and control for the data processor 200.

The control for the light source 10 includes switching the light source on and off (or switching the wavelength region of the light), and changing the light amount of the light source.

The movement mechanism 10D changes at least one of the position of the light source 10 or the orientation of the light source 10 using a known mechanism. The main controller 101 can change at least one of a relative position of the light source 10 to the iris aperture 21 and the slit 22, or a relative orientation of the light source 10 to the iris aperture 21 and the slit 22.

The control for the illumination optical system 20 includes control for a movement mechanism 22D. The movement mechanism 22D moves the slit 22 in the optical axis direction of the illumination optical system 20. The main controller 101 controls the movement mechanism 22D in accordance with the state of the subject's eye E to arrange the slit 22 at the position corresponding to the state of the subject's eye E. Examples of the state of the subject's eye E includes a shape of the fundus Ef, a dioptric power, and an axial length. The dioptric power can be obtained from a known eye refractive power measurement apparatus as disclosed in Japanese Unexamined Patent Application No.

61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 specifies the position of the slit 22 corresponding to the dioptric power by referring to the first control information, and controls the movement mechanism 22D so as to arrange the slit 22 at the specified position.

Here, as the slit 22 moves, the light amount distribution of the light passing through the aperture formed in the slit 22 changes. In this case, as described above, the main controller 101 can control the movement mechanism 10D to change at least one of the position of the light source 10 or the orientation of the light source 10.

The control for the optical scanner 30 includes control of the angle of the deflection surface deflecting the illumination light. By controlling an angle range of the deflection surface, the scan range (scan start position and scan end position) can be controlled. By controlling a change speed of the angle of the deflection surface, the scan speed can be controlled.

The control for the imaging optical system 40 includes a control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 51. Further, the main controller 101 can control the movement mechanism 47D based on a content of operation of the user using an operation unit 110 described below.

The control for the imaging device 50 includes a control for the image sensor 51. The control for the image sensor 51 includes a control for reading out the light receiving result using a rolling shutter method (for example, setting of light receiving size corresponding to the size of the illumination pattern, or the like). Further, the control for the image sensor 51 includes the reset control, the exposure control, the charge transfer control, and the output control. The time Tr required for the reset control, the time (exposure time) Te required for the exposure control, the time Tc required for the charge transfer control, and the time Tout required for the output control, etc., can be changed.

Examples of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include a specifying processing of the in-focus state.

The data processor 200 can form the light receiving image corresponding to the arbitrary opening range based on the light receiving result(s) read out from the image sensor 51 using the rolling shutter method. The data processor 200 can sequentially form light receiving light images corresponding to the opening ranges and can form an image of the subject's eye E from a plurality of formed light receiving images, as an image forming unit.

The data processor 200 includes a processor, and realizes the above functions by performing processing corresponding to the program(s) stored in the storage unit or the like.

In some embodiments, the light source 10 includes two or more light sources. In this case, each of the two or more light sources is provided corresponding to the two or more apertures formed in the iris aperture 21. The main controller 101 can change the at least one of a position of each light source or an orientation (orientation in the direction of maximum light amount distribution) of each light source, by controlling the movement mechanisms provided for each of the two or more light sources.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 200 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 200 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

As described above, in the ophthalmic apparatus 1, the slit 22 (aperture), an imaging site (fundus Ef), and the image sensor 51 (light receiving surface) are arranged at positions substantially conjugate optically each other. The ophthalmic apparatus 1 can acquire a clear image of the imaging site while suppressing the effects due to the unnecessary scattered light, by moving the light receiving opening on the image sensor 51 in conjunction with the irradiated position of the illumination light.

The data processor 200 is an example of the "image forming unit" according to the embodiments.

[Operation]

Next, the operation of the ophthalmic apparatus 1 will be described.

Figure 9A:
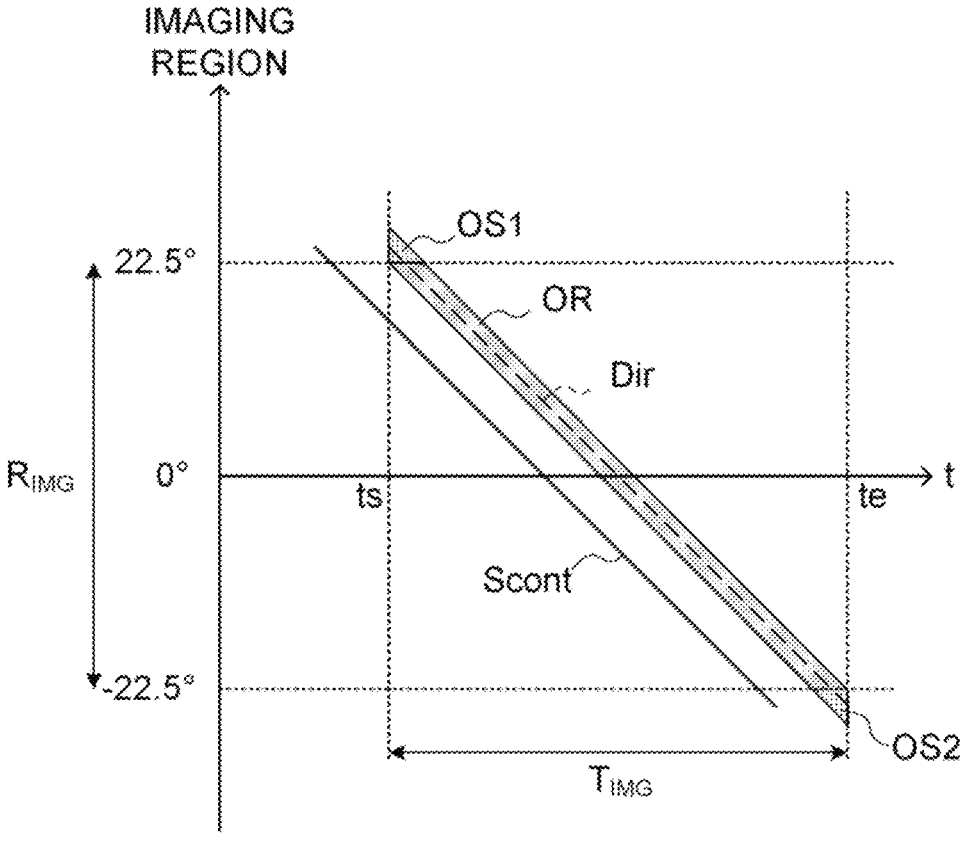
FIG. 9A is an explanatory diagram of the operation of the ophthalmic apparatus according to the embodiments.

FIG. 9A shows a diagram describing the operation of the ophthalmic apparatus 1 according to the embodiments. In FIG. 9A, the vertical axis represents the deflection angle range (±22.5°) with reference to the scan center as the imaging region on the fundus Ef. The horizontal axis represents the time axis.

The controller 100 outputs the scanner control signal Scont to the optical scanner 30, as shown in FIG. 9A. The optical scanner 30 changes the deflection surface to the deflection direction Dir corresponding to the scanner control signal Scont, after a delay of a predetermined time relative to the receiving timing of the scanner control signal Scont from the controller 100. As a result, on the fundus Ef, the illumination light is irradiated onto a region corresponding to the deflection surface of the optical scanner 30 based on the scanner control signal Scont. In the image sensor 51, in the imaging target region SR' on the light receiving surface SR, an opening range OR is opened so as to receive the returning light from the irradiated region of the illumination light on the fundus Ef using the rolling shutter method, and the light receiving result is captured in the opening range OR.

In FIG. 9A, by controlling the optical scanner 30 as shown in FIG. 7 and FIG. 8, in the first part and the last part of the imaging time (shooting time) $T_{IMG}$, the illumination light is also irradiated outside of the imaging range $R_{IMG}$ (imaging target region) (regions OS1 and OS2).

Figure 9B:
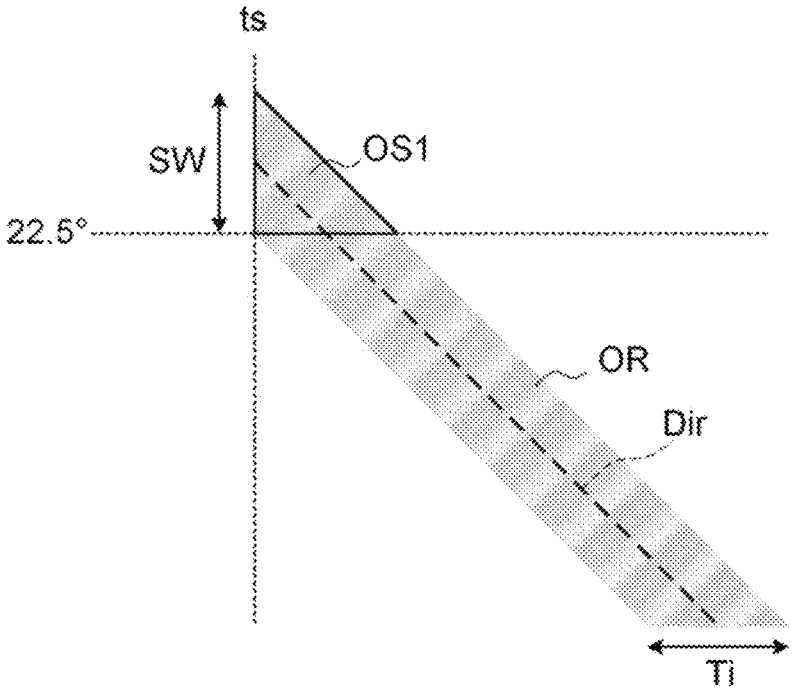
FIG. 9B is an explanatory diagram of the operation of the ophthalmic apparatus according to the embodiments.
Figure 9C:
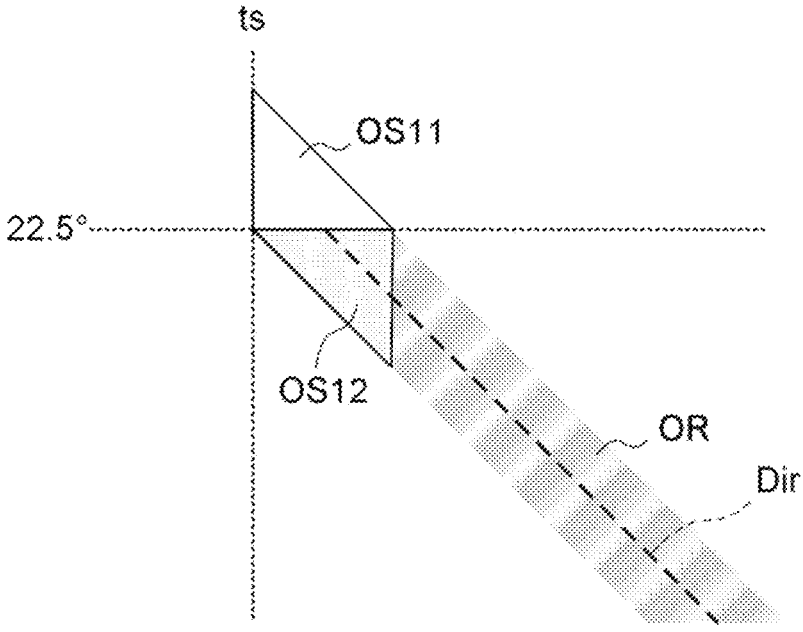
FIG. 9C is an explanatory diagram of the operation of the ophthalmic apparatus according to a comparative example of the embodiments.

FIGS. 9B and 9C show diagrams describing for comparing the embodiments with the comparative example of the embodiments. FIG. 9B represents an enlarged view of the first part of the imaging time $T_{IMG}$ in FIG. 9A. FIG. 9C represents an enlarged view of a part corresponding to FIG. 9B in the comparative example of the embodiments. Here, it is assumed that the control shown in FIG. 6 is performed in the comparative example of the embodiments. In FIGS. 9B and 9C, like reference numerals designate like parts in FIG. 9A, and the redundant explanation may be omitted as appropriate.

As shown in FIG. 9B, the width SW in the vertical direction in the region OS1 corresponds to the slit width of the illumination light, and the width Ti in the horizontal direction in the region OS1 corresponds to the irradiation time of the illumination light. In the embodiments, as shown in FIG. 9B, the region OS1 outside the imaging range is illuminated on the fundus Ef. In contrast, in the comparative example of the embodiments, as shown in FIG. 9C, the regions OS11 and OS12 on the fundus Ef are not illuminated. In particular, in the embodiments, the entire region of the imaging range is illuminated, whereas in the comparative example of the embodiments, the region OS12 within the imaging range is not illuminated.

As described above, according to the embodiments, since the control is performed as shown in FIG. 7 and FIG. 8, the variations in the irradiation times of the returning light of the illumination light for all pixel groups in the imaging target region can be made substantially equal. As a result, this allows to acquire high quality images of the fundus Ef without luminance unevenness.

MODIFICATION EXAMPLE

The configuration of the ophthalmic apparatus according to the embodiments is not limited to the configuration of the ophthalmic apparatus 1 according to the embodiment. For example, in order to reduce the influence of the operation unstable region of the optical scanner 30, the controller may control the optical scanner 30 so that the irradiated range IP' shifts from outside the imaging target region SR'.

In the following, the ophthalmic apparatus according to a modification example of the embodiments will be described focusing on differences from the ophthalmic apparatus 1 according to the embodiments.

The respective configurations of the optical system and the control system of the ophthalmic apparatus according to the modification example of the embodiments are the same as those of the optical system and the control system of the ophthalmic apparatus according to the embodiments.

The difference between the ophthalmic apparatus according to the modification example of the embodiments and the ophthalmic apparatus according to the embodiments is mainly the content of control of the optical scanner 30 by the controller.

Specifically, in the modification example of the embodiments, the controller controls the optical scanner 30 so that the irradiated range shifts from outside the imaging target region by a predetermined width greater than a width in the shift direction of the irradiated range IP' (region corresponding to the illumination region on the fundus Ef) on the light receiving surface SR of the image sensor 51.

In some embodiments, the predetermined width is a sum of the width in the shift direction of the irradiated range IP' on the light receiving surface of the image sensor 51 and a width for the number of rows corresponding to the operation unstable region of the optical scanner 30. In some embodiments, the operation unstable region of the optical scanner 30 is a nonlinear operating region of the optical scanner 30. In some embodiments, the operation unstable region of the optical scanner 30 is a region from when the scanner control signal Scont is set to when the optical scanner 30 operates in the operation stable region.

Figure 10:
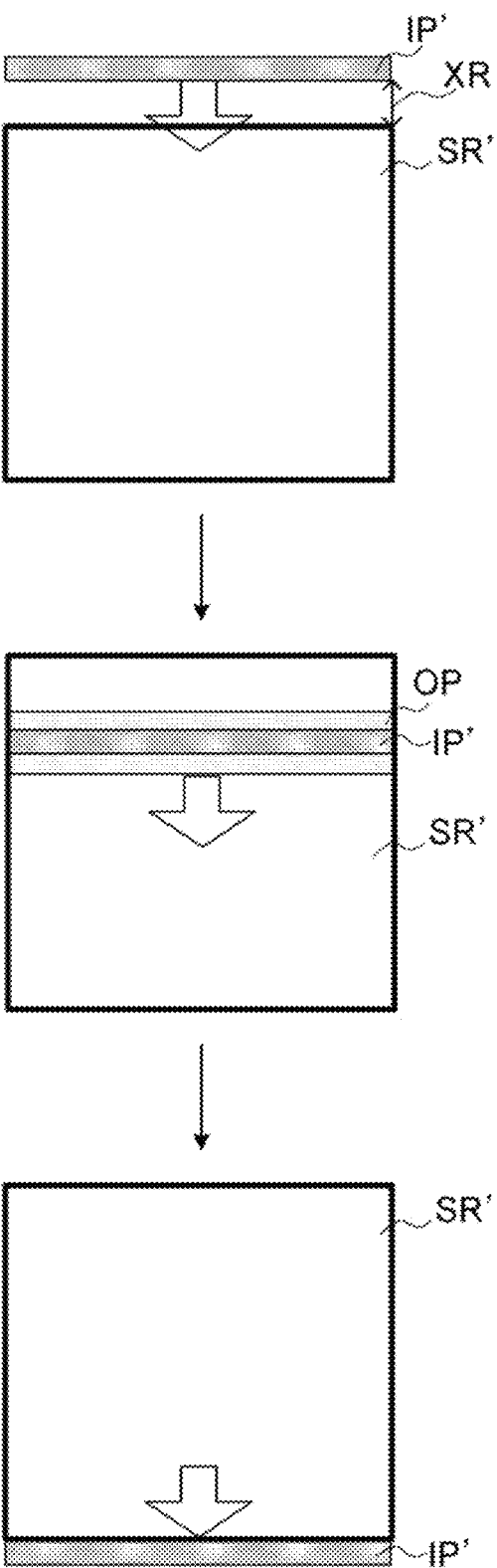
FIG. 10 is an explanatory diagram of the operation of the ophthalmic apparatus according to a modification example of the embodiments.

FIG. 10 shows a diagram explaining the operation of the ophthalmic apparatus 1 according to the modification example of the embodiments. In FIG. 10, like reference numerals designate like parts as in FIG. 7, and the same description may not be repeated.

For example, as shown in FIG. 10. compared to the case shown in FIG. 7, the irradiated range IP' is shifted outside from the outside of the imaging target region SR' further by the number XR of rows corresponding to the operation unstable region of the optical scanner 30. In other words, the controller 100 controls the optical scanner 30 so that the irradiated range IP' shifts outside from the imaging target region SR' by the sum of the width in the shift direction of the irradiated range IP' and the width corresponding to the operation unstable region of the optical scanner 30, as shown in FIG. 6. This allows to reduce the variations in the irradiation time of the returning light of the illumination light to all pixels in the imaging target region SR', without being affected by the operating unstable region of the optical scanner 30.

Figure 11:
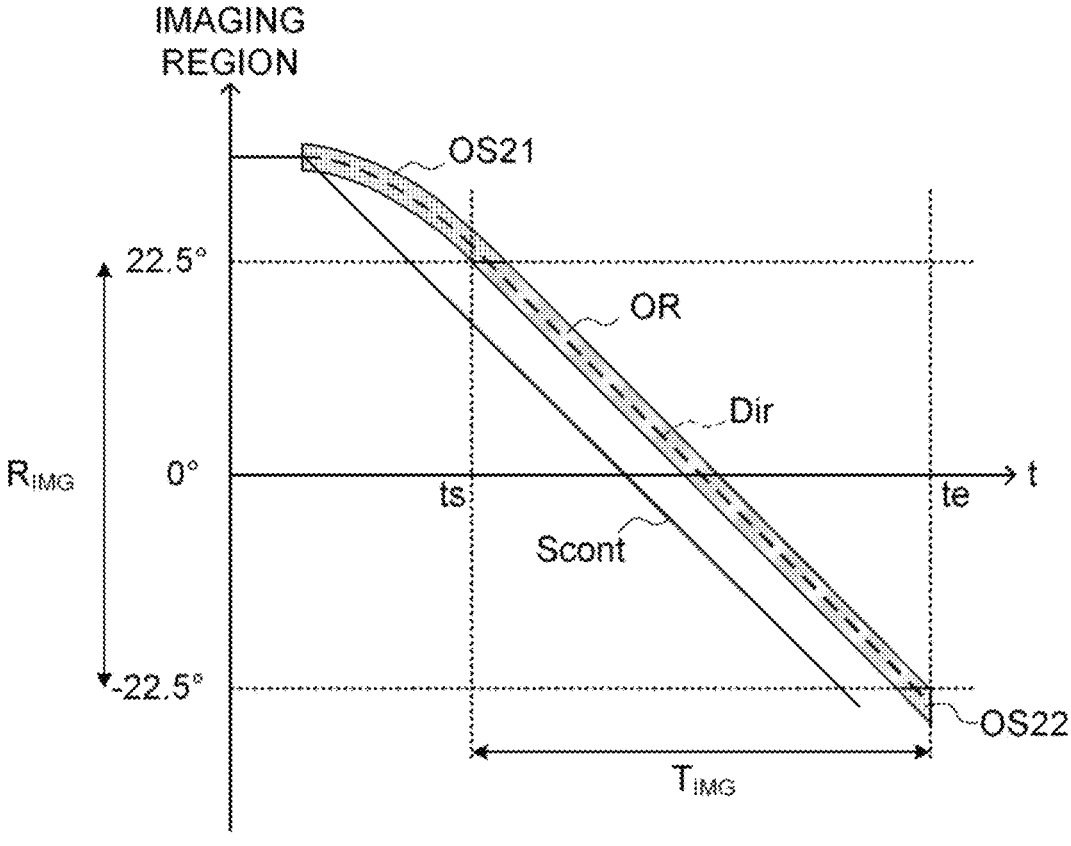
FIG. 11 is an explanatory diagram of the operation of the ophthalmic apparatus according to a modification example of the embodiments.

FIG. 11 shows a diagram explaining the operation of the ophthalmic apparatus according to the modification example of the embodiments. Like reference numerals refer to like parts in FIGS. 9A and 11, and the same description may not be repeated.

The controller 100 outputs the scanner control signal Scont to the optical scanner 30, as shown in FIG. 11. The optical scanner 30 changes the deflection surface to the deflection direction Dir corresponding to the scanner control signal Scont, after a delay of a predetermined time relative to the scanner control signal Scont from the controller 100. In the image sensor 51, in the imaging target region SR' on the light receiving surface SR, an opening range OR is opened so as to receive the returning light from the irradiated region of the illumination light on the fundus Ef using the rolling shutter method, and the light receiving result is captured in the opening range OR.

In FIG. 11, by controlling the optical scanner 30 as shown in FIG. 10, in the first part and the last part of the imaging time $T_{IMG}$, the illumination light is also irradiated outside of the imaging range $R_{IMG}$ (imaging target region) (regions OS21 and OS22).

As described above, according to the modification example of the embodiments, this allows to reduce the variations in the irradiation time of the returning light of the illumination light to all pixels in the imaging target region SR', without being affected by the operating unstable region of the optical scanner 30. As a result, this allows to acquire high quality images of the fundus Ef, without being affected by the operating unstable region of the optical scanner 30.

[Actions and Effects]

The actions and the effects of an ophthalmic apparatus, a method of controlling the same, and a program according to the embodiments will be described.

An ophthalmic apparatus (1) according to some embodiments includes an illumination optical system (20), an optical scanner (30), an imaging optical system (40), a controller (100, main controller 101), and an image forming unit (data processor 200). The illumination optical system is configured to generate slit-shaped illumination light. The optical scanner is configured to deflect the illumination light to guide the illumination light to a fundus (Ef) of a subject's eye (E). The imaging optical system is configured to guide returning light of the illumination light from the fundus to an image sensor (51). The controller is configured to control the optical scanner. The image forming unit is configured to form an image of the fundus based on a light receiving result captured in an imaging target region (SR') on a light receiving surface (SR) of the image sensor. The image sensor is configured to capture the light receiving result in an opening region (opening range OP) on the light receiving surface using a rolling shutter method, the opening region corresponding to an illumination region of the illumination light on the fundus, the illumination region being moved in a predetermined scan direction by the optical scanner. The controller is configured to control the optical scanner so that irradiation times of the returning light at a plurality of light receiving elements in the imaging target region are substantially equal.

According to such a configuration, the variations in the irradiation time of the returning light can be reduced in the imaging target region. This allows to acquire high quality images of the subject's eye (fundus) without luminance unevenness, in a short imaging time.

In some embodiments, the image sensor includes a plurality of light receiving elements arranged in a column direction, with light receiving element groups arranged in a row direction orthogonal to a shift direction of the opening region shifted corresponding to the illumination region. A width in the shift direction of an irradiated range (IP') on the light receiving surface corresponding to the illumination region has a width for two or more rows. The controller is configured to control the optical scanner so that the irradiated range shifts from outside the imaging target region in the shift direction in units of a predetermined number of rows.

According to such a configuration, the variations in the irradiation time in the imaging target region can be reduced with a simple control, without adding new configurations.

In some embodiments, the controller is configured to control the optical scanner so that the irradiated range shifts from outside the imaging target region by a width for at least one row.

According to such a configuration, the variations in the irradiation time of the returning light in the imaging target region can be reduced. Thereby, high quality image of the subject's eye can be easily acquired in a short imaging time.

In some embodiments, the controller is configured to control the optical scanner so that the irradiated range shifts from outside the imaging target region by the width in the shift direction of a region corresponding to the illumination region on the light receiving surface.

According to such a configuration, since the irradiation times of the returning light can be made equal at all light receiving elements in the imaging target region with a simple control, high quality images of the subject's eye can be easily acquired in a short imaging time.

In some embodiments, the controller is configured to control the optical scanner so that the irradiated range shifts from outside the imaging target region by a predetermined width greater than the width in the shift direction of a region corresponding to the illumination region on the light receiving surface.

According to such a configuration, high quality images of the subject's eye can be easily acquired in a short imaging time, while reducing the influence of the operation unstable region of the optical scanner.

In some embodiments, the predetermined width is a sum of the width in the shift direction of the region corresponding to the illumination region on the light receiving surface and a width for the number of rows corresponding to an operation unstable region of the optical scanner.

According to such a configuration, the high quality images of the subject's eye can be easily acquired in a short imaging time, without being affected at all by the operation unstable region of the optical scanner.

In some embodiments, the image sensor is a CMOS image sensor.

According to such a configuration, the variations in the irradiation time of the returning light can be reduced in the imaging target region with a simple configuration at low cost.

A method of controlling an ophthalmic apparatus (1) is a method of controlling the ophthalmic apparatus including: an illumination optical system (20) configured to generate slit-shaped illumination light; an optical scanner (30) configured to deflect the illumination light to guide the illumination light to a fundus (Ef) of a subject's eye (E); an imaging optical system (40) configured to guide returning light of the illumination light from the fundus to an image sensor (51), the image sensor being configured to capture a light receiving result on an opening region on the light receiving surface (SR), the opening region corresponding to the illumination region of the illumination light on the fundus, the illumination region being moved in a predetermined scan direction by the optical scanner; and a controller (100, main controller 101) configured to control the optical scanner. The method of controlling the ophthalmic apparatus includes: a control step of controlling the optical scanner so that irradiation times of the returning light at a plurality of light receiving elements in the imaging target region (SR') on the light receiving surface of the image sensor are substantially equal; and an image forming step of forming an image of the fundus based on a light receiving result captured in the imaging target region.

According to such a method, the variations in the irradiation time of the returning light can be reduced in the imaging target region. This allows to acquire high quality images of the subject's eye (fundus) without luminance unevenness, in a short imaging time.

In some embodiments, the image sensor includes a plurality of light receiving elements arranged in a column direction, with light receiving element groups arranged in a row direction orthogonal to a shift direction of an opening range shifted corresponding to the illumination region. A width in the shift direction of an irradiated range (IP') on the light receiving surface corresponding to the illumination region has a width for two or more rows. The control step is performed to control the optical scanner so that the irradiated range shifts from outside the imaging target region in the shift direction in units of a predetermined number of rows.

According to such a method, the variations in the irradiation time in the imaging target region can be reduced with a simple control, without adding new configurations.

In some embodiments, the control step is performed to control the optical scanner so that the irradiated range shifts from outside the imaging target region by a width for at least one row.

According to such a method, the variations in the irradiation time of the returning light in the imaging target region can be reduced. Thereby, high quality image of the subject's eye can be easily acquired.

In some embodiments, the control step is performed to control the optical scanner so that the irradiated range shifts from outside the imaging target region by the width in the shift direction of a region corresponding to the illumination region on the light receiving surface.

According to such a method, since the irradiation times of the returning light can be made equal at all light receiving elements in the imaging target region with a simple control, high quality images of the subject's eye can be easily acquired in a short imaging time.

In some embodiments, the control step is performed to control the optical scanner so that the irradiated range shifts from outside the imaging target region by a predetermined width greater than the width in the shift direction of a region corresponding to the illumination region on the light receiving surface.

According to such a method, high quality images of the subject's eye can be easily acquired in a short imaging time, while reducing the influence of the operation unstable region of the optical scanner.

In some embodiments, the predetermined width is a sum of the width in the shift direction of the region corresponding to the illumination region on the light receiving surface and a width for the number of rows corresponding to an operation unstable region of the optical scanner.

According to such a method, the high quality images of the subject's eye can be easily acquired in a short imaging time, without being affected at all by the operation unstable region of the optical scanner.

In some embodiments, the image sensor is a CMOS image sensor.

According to such a method, the variations in the irradiation time of the returning light can be reduced in the imaging target region at low cost.

A program according to some embodiments causes a computer to execute each step of the method of controlling the ophthalmic apparatus described any one of the above.

According to such a program, the variations in the irradiation time of the returning light can be reduced in the imaging target region. This allows to acquire high quality images of the subject's eye (fundus) without luminance unevenness, in a short imaging time.

The above-described some embodiments or the modification examples thereof are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

20

What is claimed is:
1. An ophthalmic apparatus, comprising:
an illumination optical system including a slit and configured to generate slit-shaped illumination light by irradiating light from a light source onto the slit, the slit being movable in an optical axis direction of the illumination optical system and capable of being arranged at a position substantially conjugate optically to a fundus of a subject's eye, and at least one of a relative position of the light source to the slit, or a relative orientation of the light source to the slit is configured to be changeable as the slit moves;
an optical scanner configured to deflect the illumination light to guide the illumination light to the fundus of the subject's eye;
an imaging optical system configured to guide returning light of the illumination light from the fundus to an image sensor;
a controller configured to control the optical scanner; and
an image forming unit configured to form an image of the fundus based on a light receiving result captured in an imaging target region on a light receiving surface of the image sensor, wherein
the image sensor is configured to capture the light receiving result in an opening region on the light receiving surface using a rolling shutter method, the opening region corresponding to an illumination region of the illumination light on the fundus, the illumination region being moved in a predetermined scan direction by the optical scanner,
the controller is configured to control the optical scanner so that irradiation times of the returning light at a plurality of light receiving elements in the imaging target region are equal,
the image sensor includes a plurality of light receiving elements arranged in a column direction, with light receiving element groups arranged in a row direction orthogonal to a shift direction of the opening region shifted corresponding to the illumination region,
a width in the shift direction of an irradiated range on the light receiving surface corresponding to the illumination region has a width for two or more rows,
the controller is configured to control the optical scanner so that the irradiated range shifts from outside the imaging target region in the shift direction in units of a predetermined number of rows,
the controller is configured to control the optical scanner so that the irradiated range shifts from outside the imaging target region by a predetermined width greater than the width in the shift direction of a region corresponding to the illumination region on the light receiving surface, and
the predetermined width is a sum of the width in the shift direction of the region corresponding to the illumination region on the light receiving surface and a width for the number of rows corresponding to an operation unstable region of the optical scanner.
2. The ophthalmic apparatus of claim 1, wherein
the controller is configured to control the optical scanner so that the irradiated range shifts from outside the imaging target region by a width for at least one row.
3. The ophthalmic apparatus of claim 1, wherein
the image sensor is a CMOS image sensor.

* * * * *